US012579711B2

(12) United States Patent
Kubota et al.

(10) Patent No.: US 12,579,711 B2
(45) Date of Patent: Mar. 17, 2026

(54) ENDOSCOPE PROCESSOR, ENDOSCOPE APPARATUS, AND DIAGNOSTIC IMAGE DISPLAY METHOD TO GENERATE PARTIAL TRANSPARENT IMAGE

(71) Applicant: OLYMPUS MEDICAL SYSTEMS CORP., Tokyo (JP)

(72) Inventors: Akihiro Kubota, Hachioji (JP); Yamato Kanda, Hachioji (JP); Yasunori Morita, Hachioji (JP); Naohisa Takabatake, Hachioji (JP); Takashi Kono, Hachioji (JP); Hiroki Taniguchi, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 177 days.

(21) Appl. No.: 18/224,651

(22) Filed: Jul. 21, 2023

(65) Prior Publication Data

US 2023/0360298 A1     Nov. 9, 2023

Related U.S. Application Data

(63) Continuation of application No. PCT/JP2021/025205, filed on Jul. 2, 2021.

(51) Int. Cl.
*H04N 7/18*          (2006.01)
*A61B 1/00*          (2006.01)
(Continued)

(52) U.S. Cl.
CPC ........ *G06T 11/60* (2013.01); *A61B 1/000096* (2022.02); *A61B 1/0638* (2013.01);
(Continued)

(58) Field of Classification Search
CPC ....................................................... G06T 11/60
(Continued)

(56) References Cited

U.S. PATENT DOCUMENTS

| | | | | |
|---|---|---|---|---|
| 7,298,883 B2 * | 11/2007 | Giger | .................. | G06F 18/2321 |
| | | | | 600/443 |
| 2012/0121144 A1 * | 5/2012 | Tanaka | .................. | G06T 7/0012 |
| | | | | 382/128 |

(Continued)

FOREIGN PATENT DOCUMENTS

| | | |
|---|---|---|
| EP | 3593704 A1 | 1/2020 |
| JP | 2008086605 A | 4/2008 |

(Continued)

OTHER PUBLICATIONS

International Search Report dated Sep. 21, 2021 issued in PCT/JP2021/025205.

*Primary Examiner* — Leron Beck
(74) *Attorney, Agent, or Firm* — Scully, Scott, Murphy & Presser, P.C.

(57) ABSTRACT

An endoscope processor includes a processor. The processor discriminates, in first image information acquired by applying first illumination light, between first region image information constituted of an object of an interest subject and second region image information constituted of an object of a non-interest subject, generates third region image information of a region in second image information acquired by applying second illumination light, the region including at least a part of a region of the second region image information, the second illumination light having a wavelength different from a wavelength of the first illumination light and passing through the object of the non-interest subject, and combines the first region image information and the third region image information, to generate a partial transparent
(Continued)

WHITE LIGHT IMAGE

SPECIAL LIGHT IMAGE

DISPLAY IMAGE image in which the object of the non-interest subject of the first image information is made transparent.

17 Claims, 14 Drawing Sheets

(51) Int. Cl.

| | |
|---|---|
| *A61B 1/06* | (2006.01) |
| *G06T 7/00* | (2017.01) |
| *G06T 7/11* | (2017.01) |
| *G06T 11/60* | (2006.01) |

(52) U.S. Cl.

CPC .............. *G06T 7/0012* (2013.01); *G06T 7/11* (2017.01); *G06T 2207/10024* (2013.01); *G06T 2207/10068* (2013.01); *G06T 2207/10152* (2013.01); *G06T 2207/30096* (2013.01); *G06T 2210/41* (2013.01); *G06T 2210/62* (2013.01)

(58) Field of Classification Search

USPC .......................................................... 348/68

See application file for complete search history.

(56) References Cited

U.S. PATENT DOCUMENTS

| | | | | |
|---|---|---|---|---|
| 2012/0177259 | A1* | 7/2012 | Hirota | ........................ G06T 7/12 382/128 |
| 2012/0328175 | A1* | 12/2012 | Watanabe | ................ A61B 1/05 382/132 |
| 2014/0213871 | A1 | 7/2014 | Watanabe | |
| 2014/0270377 | A1* | 9/2014 | Kanda | .................... A61B 1/041 382/103 |
| 2017/0209031 | A1* | 7/2017 | Nakamura | ....... A61B 1/000094 |
| 2019/0069769 | A1 | 3/2019 | Kubo | |
| 2020/0015927 | A1 | 1/2020 | Ichiki et al. | |
| 2020/0138265 | A1* | 5/2020 | Endo | .................... G06T 7/0012 |
| 2020/0214547 | A1* | 7/2020 | Aoyama | ............. A61B 1/0646 |
| 2020/0242764 | A1* | 7/2020 | Aoyama | ............. A61B 5/7275 |
| 2020/0397278 | A1 | 12/2020 | Kubo et al. | |
| 2021/0076917 | A1* | 3/2021 | Kamon | ................ A61B 1/0661 |
| 2021/0224989 | A1* | 7/2021 | Aoyama | ............... G16H 30/40 |
| 2021/0228068 | A1* | 7/2021 | Chiba | ................ A61B 1/00043 |
| 2021/0233298 | A1* | 7/2021 | Usuda | ...................... H04N 7/18 |

FOREIGN PATENT DOCUMENTS

| | | |
|---|---|---|
| JP | 2014221168 A | 11/2014 |
| JP | 6246431 B2 | 12/2017 |
| WO | 2013051431 A1 | 4/2013 |
| WO | 2017199509 A1 | 11/2017 |
| WO | 2018163644 A1 | 9/2018 |
| WO | 2019171615 A1 | 9/2019 |
| WO | 2020045619 A1 | 3/2020 |

\* cited by examiner

Figure 8:
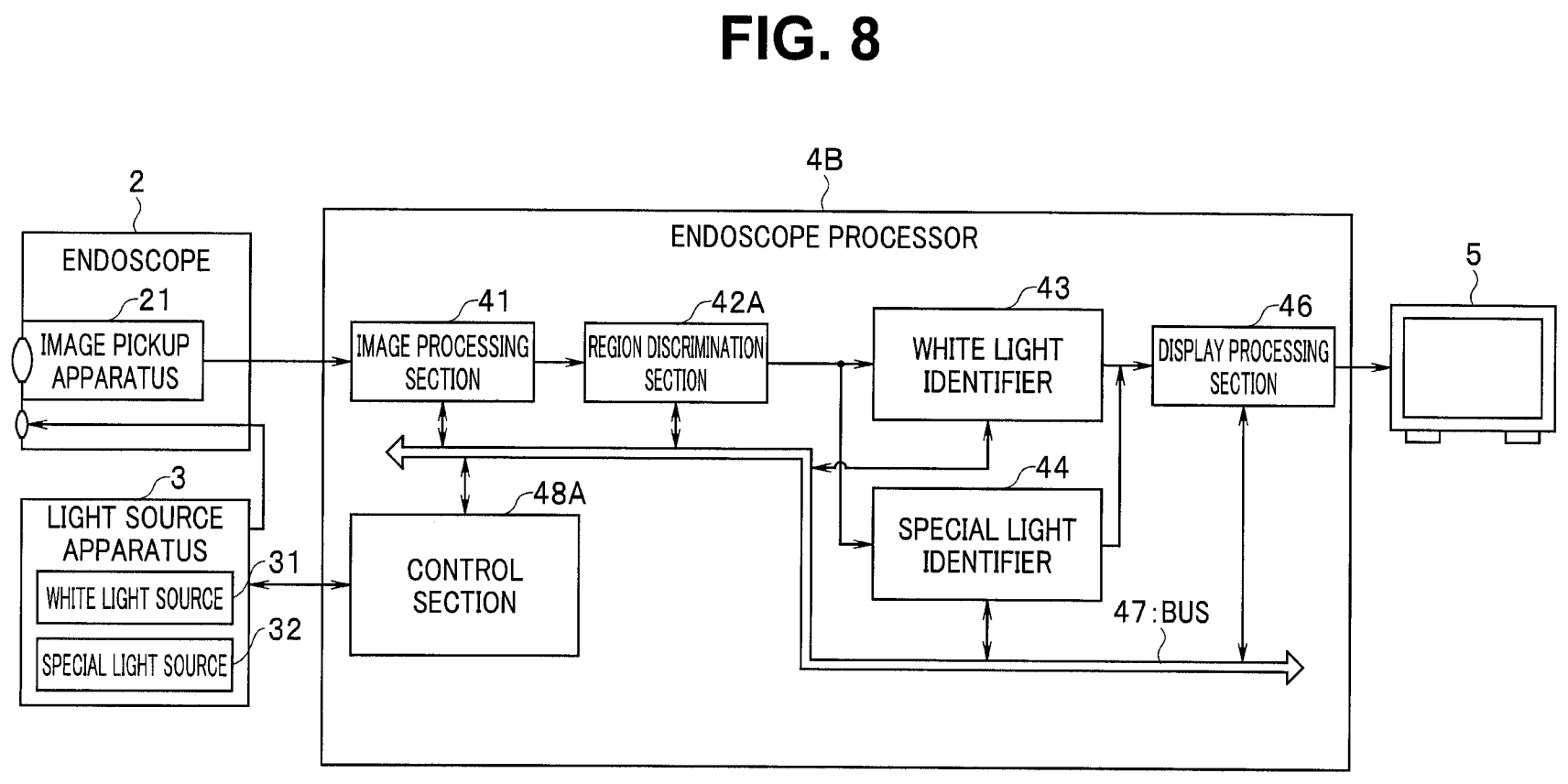

ENDOSCOPE PROCESSOR 4B

DISPLAY PROCESSING SECTION 46

WHITE LIGHT IDENTIFIER 43

SPECIAL LIGHT IDENTIFIER 44

47 : BUS

REGION DISCRIMINATION SECTION 42A

IMAGE PROCESSING SECTION 41

CONTROL SECTION 48A

ENDOSCOPE 2

IMAGE PICKUP APPARATUS 21

LIGHT SOURCE APPARATUS 3

WHITE LIGHT SOURCE 31

SPECIAL LIGHT SOURCE 32

5

ENDOSCOPE PROCESSOR, ENDOSCOPE APPARATUS, AND DIAGNOSTIC IMAGE DISPLAY METHOD TO GENERATE PARTIAL TRANSPARENT IMAGE

CROSS-REFERENCE TO RELATED APPLICATION

This application is a continuation application of PCT/JP2021/025205 filed on Jul. 2, 2021, the entire contents of which are incorporated herein by this reference.

BACKGROUND OF THE INVENTION

1. Field of the Invention

The present invention relates to an endoscope processor, an endoscope apparatus, and a diagnostic image display method.

2. Description of the Related Art

Conventionally, endoscopes have been widely used in medical fields and industrial fields. In the medical fields, for example, an operator looks at an endoscopic image of an inside of a subject to be examined, which is displayed on a display apparatus, to thereby be capable of finding and distinguishing a lesion part and performing treatment on the lesion part by using a treatment instrument.

In recent years, in order to prevent an operator from overlooking a lesion part, a technique of computer-assisted image diagnosis (CAD: Computer Aided Detection/Diagnosis) has been developed for showing a position of a lesion candidate and displaying distinguishing information on a moving image acquired by an endoscope. For example, the publication of Japanese Patent No. 6246431 proposes an endoscope apparatus configured to notify, if a lesion part is found with the CAD, an operator of a position where the lesion part exists by highlighting the position with a marker such as a frame on an endoscopic image.

In addition, Japanese Patent Application Laid-Open Publication No. 2014-221168 proposes an endoscope system configured to allow various kinds of structure including blood vessels which exist under a non-interest substance such as residue or the like to be seen through by using bluish special light.

SUMMARY OF THE INVENTION

An endoscope processor according to one aspect of the present invention includes a processor. The processor is configured to: discriminate, in first image information acquired by applying first illumination light, between first region image information constituted of an object of an interest subject and second region image information constituted of an object of a non-interest subject; generate third region image information of a region in second image information acquired by applying second illumination light, the region including at least a part of a region of the second region image information, the second illumination light having a wavelength different from a wavelength of the first illumination light and passing through the object of the non-interest subject; and combine the first region image information and the third region image information, to generate a partial transparent image in which the object of the non-interest subject in the first image information is made transparent.

Further, an endoscope apparatus according to one aspect of the present invention includes: a light source apparatus configured to be capable of emitting first illumination light and second illumination light, the second illumination light having a wavelength different from a wavelength of the first illumination light and passing through an object of a non-interest subject; an endoscope including an image pickup apparatus configured to acquire first image information by the first illumination light being applied by the light source apparatus and to acquire second image information by the second illumination light being applied by the light source apparatus; an endoscope processor including a processor, the processor being configured to: discriminate, in the first image information, between first region image information constituted of an object of an interest subject and second region image information constituted of an object of a non-interest subject; generate third region image information of a region in the second image information, the region including at least a part of a region of the second region image information; and combine the first region image information and the third region image information, to generate a partial transparent image in which the object of the non-interest subject in the first image information is made transparent; and a monitor configured to display the partial transparent image.

Furthermore, a diagnostic image display method according to one aspect of the present invention includes: discriminating, in first image information acquired by applying first illumination light, between first region image information constituted of an object of an interest subject and second region image information constituted of an object of a non-interest subject; generating third region image information of a region in second image information acquired by applying second illumination light, the region including at least a part of a region of the second region image information, the second illumination light having a wavelength different from a wavelength of the first illumination light and passing through the object of the non-interest subject; and combining the first region image information and the third region image information, to generate a partial transparent image in which the object of the non-interest subject in the first image information is made transparent.

BRIEF DESCRIPTION OF THE DRAWINGS

FIG. 2 is a block diagram showing an example of the configuration of the endoscope apparatus 1.

FIG. 3 is a block diagram showing an example of another configuration of the endoscope apparatus 1.

FIG. 6 is a view showing an example of display processing in a case where a white light image includes residue, blood, and the like.

FIG. 8 is a block diagram showing an example of a configuration of an endoscope apparatus 1 according to a second embodiment of the present invention.

DETAILED DESCRIPTION OF THE PREFERRED EMBODIMENT(S)

Figure 1:
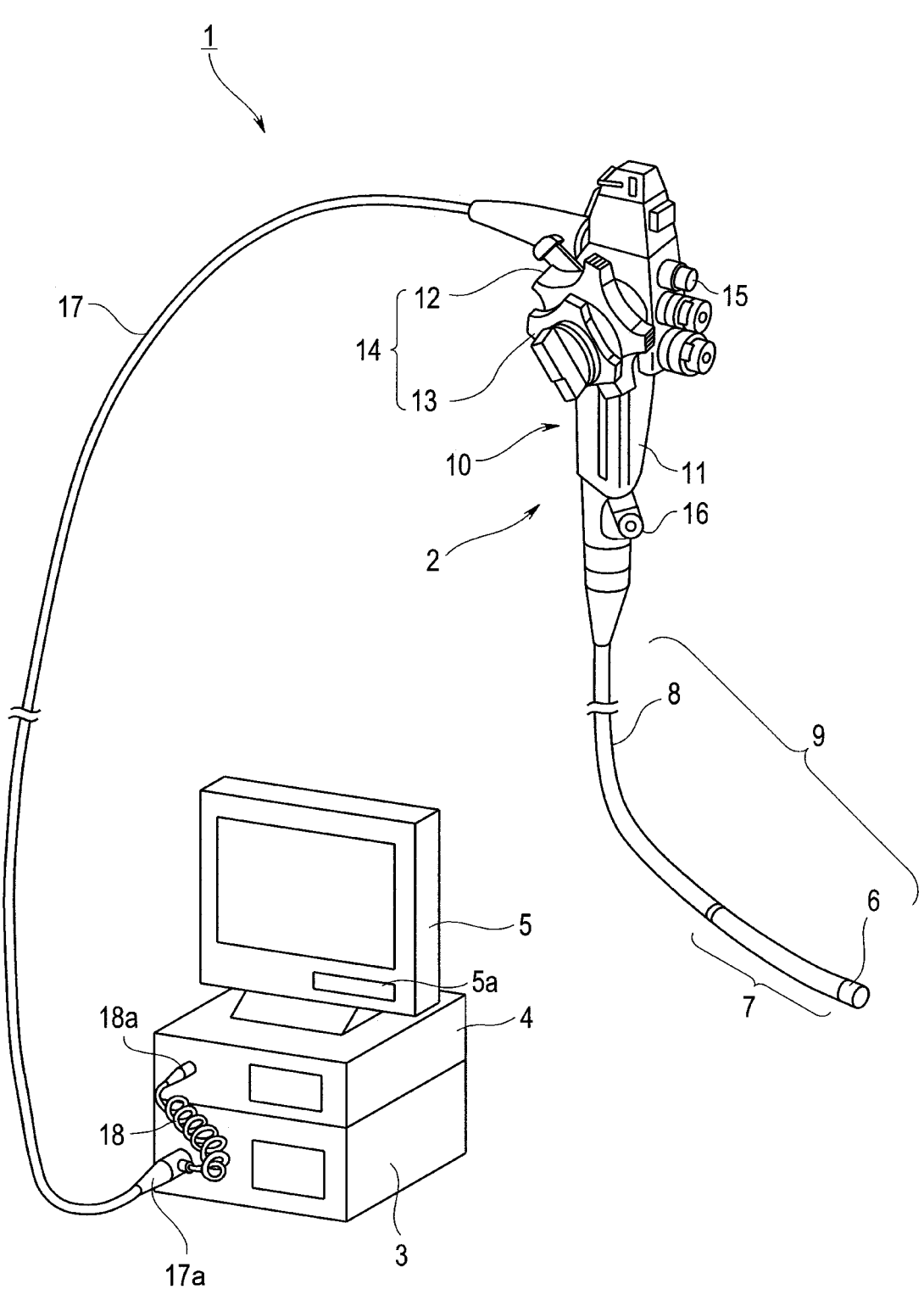
FIG. 1 is a perspective view showing an example of a configuration of an endoscope apparatus 1.

Hereinafter, embodiments of the present invention will be described with reference to drawings. However, the present invention is not limited by the embodiments to be described below. Note that the same or corresponding elements are attached with the same reference signs as appropriate in the drawings.

FIRST EMBODIMENT

FIG. 1 is a perspective view showing an example of a configuration of an endoscope apparatus 1. The first endoscope apparatus 1 of the present embodiment includes an endoscope 2, a light source apparatus 3, an endoscope processor 4, and a monitor 5.

The endoscope 2 includes: an elongated insertion portion 9 configured to be inserted into a subject to be examined; an operation portion 10 for performing various kinds of operations related to the endoscope 2; and a universal cable 17 for connecting the endoscope 2 to the light source apparatus 3 and the endoscope processor 4.

The insertion portion 9 includes, in the following order from the distal end toward the proximal end side, a distal end portion 6, a bending portion 7, and a flexible tube portion 8. The distal end portion 6, although illustration thereof is omitted, includes an illumination window through which illumination light is emitted to a subject to be examined, and an observation window on which return light from the subject to be examined is incident. The endoscope 2 of the present embodiment is configured as an electronic endoscope, and includes an image pickup apparatus 21 (see FIG. 2) in the distal end portion 6. The image pickup apparatus 21 includes an image pickup optical system and an image pickup device. The image pickup optical system forms an image of the light incident from the observation window on the image pickup device, as an object image. The image pickup device is an image sensor such as a CCD (Charge Coupled Device), CMOS (Complementary Metal Oxide Semiconductor), or the like. The image pickup device photoelectrically converts the object image to generate an image pickup signal and outputs the generated image pickup signal. The image pickup signal is transmitted to the endoscope processor 4 via a signal line.

The bending portion 7 is a bendable part provided continuously with the proximal end side of the distal end portion 6 and is configured to bend, to thereby change the direction in which the distal end portion 6 is oriented. The direction of the distal end portion 6 is changed, to thereby change the observation site of the subject to be examined or improve the insertion performance of the endoscope 2.

The flexible tube portion 8 is a flexible part provided continuously with the proximal end side of the bending portion 7.

In the insertion portion 9 and the operation portion 10, a bending wire for bending the bending portion 7 and a treatment instrument channel through which a treatment instrument is to be inserted are disposed. In addition, inside the insertion portion 9, the operation portion 10, and the universal cable 17 of the endoscope 2, the above-described signal line connected to the image pickup device and a light guide for transmitting the illumination light are disposed.

The operation portion 10 is provided with a bending operation portion 14 for performing bending operation of the bending portion 7 via the bending wire, various kinds of switches including a focus switch 15, and the like. The bending operation portion 14 is provided with a UD bending operation knob 12 and an RL bending operation knob 13. The UD bending operation knob 12 is configured to bend the bending portion 7 in up and down directions. The RL bending operation knob 13 is configured to bend the bending portion 7 in left and right directions. The bending portion 7 can be bent in oblique directions by the bending in the up and down directions and the bending in the left and right directions being combined.

The operation portion 10 includes, on the distal end side thereof, a grasping portion 11 configured to allow an operator to grasp the endoscope 2 with his or her hand, and a treatment instrument channel insertion port 16 which serves as a proximal end side opening of the above-described treatment instrument channel.

The universal cable 17 is extended from a side surface on the proximal end side of the operation portion 10, for example. The universal cable 17 includes, at the proximal end thereof, a scope connector 17a. The scope connector 17a detachably connects the endoscope 2 to the light source apparatus 3. The scope connector 17a is connected to the light source apparatus 3, to thereby enable transmission of the illumination light by the light guide.

From a side surface of the scope connector 17a, a coil-shaped coil cable 18 is extended. A scope connector 18a provided at an extension end of the coil cable 18 is detachably connected to the endoscope processor 4. The scope connector 18a is connected to the endoscope processor 4, to thereby establish the electrical connection of the image pickup device to the endoscope processor 4.

The endoscope processor 4 is electrically connected to the monitor 5 as a display apparatus. The endoscope processor 4 processes an image pickup signal outputted from the image pickup device of the endoscope 2, to generate image-for-display information. The image-for-display information is outputted from the endoscope processor 4 to the monitor 5, to be displayed, as a display image including an endoscopic image, on the monitor 5. The monitor 5 is provided with a speaker 5a for outputting a voice.

Figure 2:
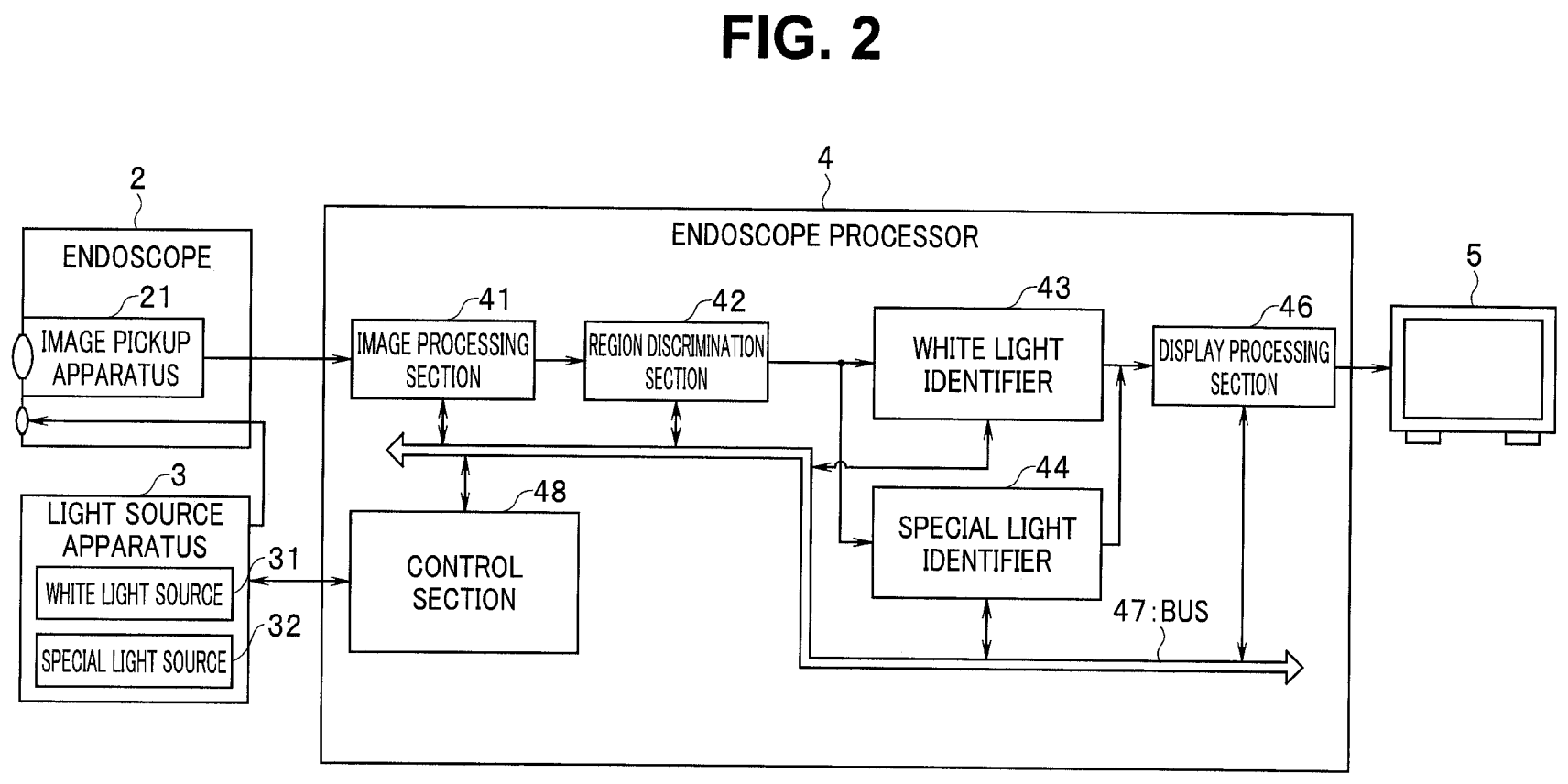

FIG. 2 is a block diagram showing an example of a configuration of the endoscope apparatus 1.

The endoscope 2 includes the image pickup apparatus 21, as described above. The image pickup apparatus 21 is configured to acquire first image information (white light image information to be described later) by applying first illumination light from the light source apparatus 3, and to acquire second image information (special light image information to be described later) by applying second illumination light from the light source apparatus 3.

The light source apparatus 3 is capable of applying the first illumination light and the second illumination light. The second illumination light has a wavelength different from that of the first illumination light. The light source apparatus 3 of the present embodiment is provided with a white light source 31 and a special light source 32. The white light source 31 emits white light for observation. The special light source 32 emits special light having a spectrum different from that of the white light. The white light is the first illumination light, and the special light is the second illumination light.

Specifically, the light source apparatus 3 is provided with a plurality of light sources configured to respectively emit light of respective colors such as R (red), G (green), B (blue), V (violet), A (amber), etc. The light sources of respective colors are combined to configure the above-described white light source 31 and the special light source 32.

The light source apparatus 3 includes a light emitting device such as an LED (Light Emitting Diode), an LD (Laser Diode), or the like, for example. As an example, the light source apparatus 3 includes a V-LED that emits violet (V) light having a center wavelength of about 405 nm, a B-LED that emits blue (B) light having a center wavelength of about 445 nm, a G-LED that emits green (G) light having a center wavelength of about 540 nm, and an R-LED that emits red (R) light having a center wavelength of about 630 nm. In addition, the light source apparatus 3 is provided with, as appropriate, a prism, a mirror, an optical fiber, or an optical filter or the like for adjusting the wavelength band or the light quantity.

The light source apparatus 3 of the present embodiment is configured to emit, for example, the white light and the special light in turn for each frame. This allows the image pickup apparatus 21 to acquire white light image information (hereinafter referred to as white light image) and special light image information (hereinafter referred to as special light image) in sequence, that is, in such a repeated manner as to acquire a white light image again after a special light image.

The endoscope processor 4 includes an image processing section 41, a region discrimination section 42, a white light identifier 43, a special light identifier 44, a display processing section 46, a bus 47, and a control section 48.

Note that FIG. 2 shows an example including the two identifiers, i.e., the white light identifier 43 and the special light identifier 44. However, three or more identifiers may be provided.

Figure 3:
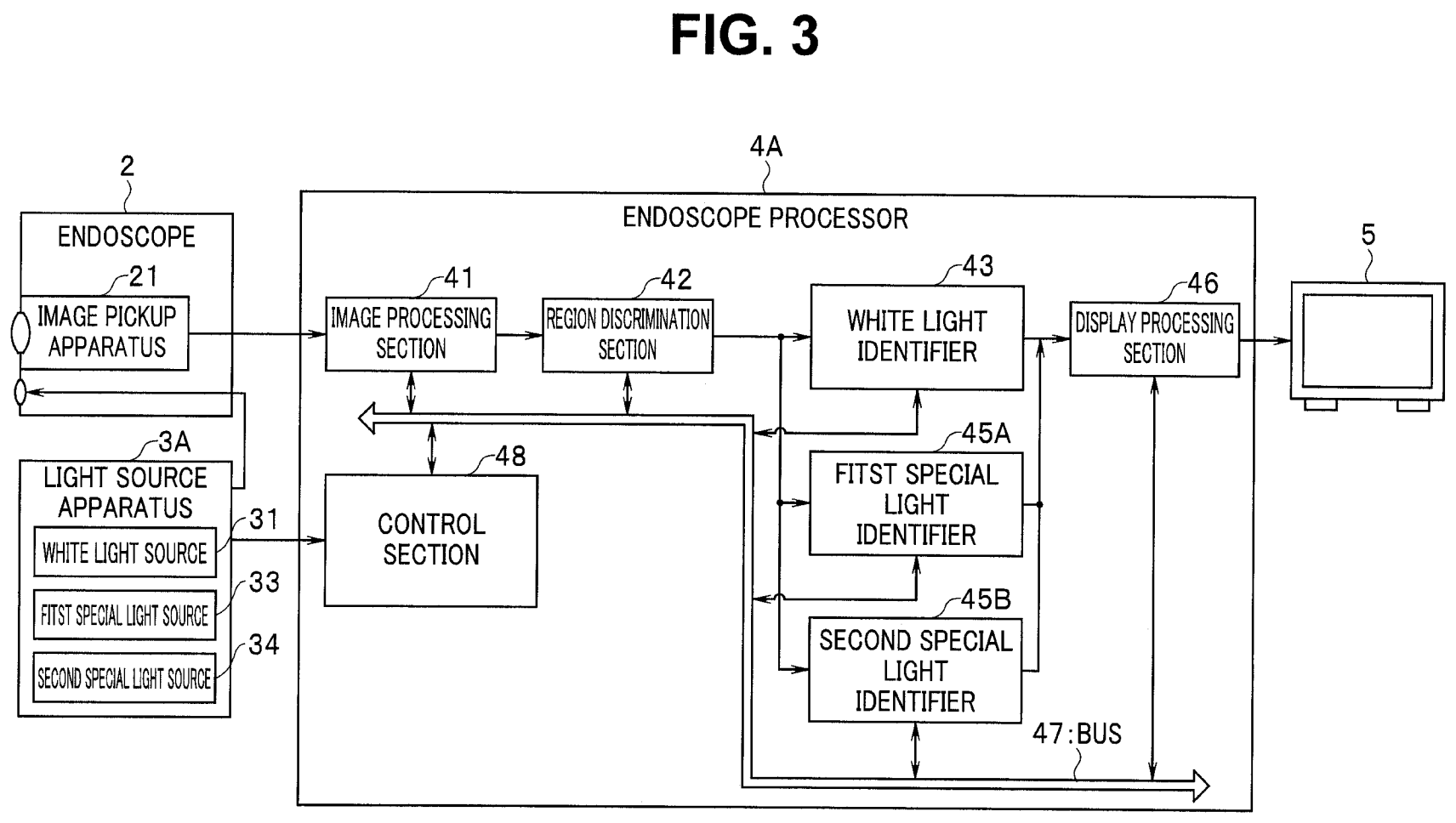

FIG. 3 is a block diagram showing an example of another configuration of the endoscope apparatus 1. An endoscope processor 4A in FIG. 3 has a configuration in which three identifiers are provided. The endoscope processor 4A is configured by using a first special light identifier 45A and a second special light identifier 45B, instead of the special light identifier 44 in FIG. 2. Furthermore, a light source apparatus 3A is configured by using a first special light source 33 that outputs first special light, and a second special light source 34 that outputs second special light, instead of the special light source 32 in FIG. 2.

Alternatively, one identifier having a plurality of identification functions may be provided to cause the one identifier to function both as the white light identifier 43 and the special light identifier 44 by switching the identification functions.

Figure 4:
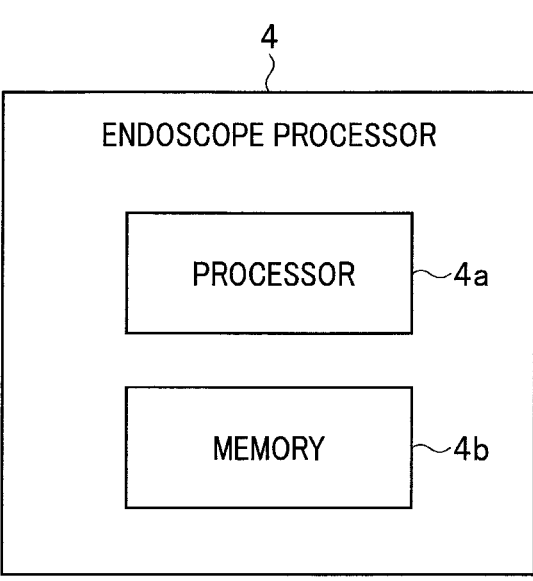
FIG. 4 is a block diagram showing an electrical configuration example of an endoscope processor 4.

FIG. 4 is a block diagram showing an electrical configuration example of the endoscope processor 4. Although FIG. 2 shows a functional configuration of the endoscope processor 4, the endoscope processor 4 includes, as the electrical configuration, a processor 4a and a memory 4b, for example.

The processor 4a includes, for example, an ASIC (Application Specific Integrated Circuit) including a CPU (Central Processing Unit) and the like, or an FPGA (Field Programmable Gate Array). The memory 4b is a storage medium such as a RAM (Random Access Memory), a flush memory, a disk storage medium, or the like. The memory 4b includes a non-transitory computer readable storage medium that records a processing program.

The processor 4a reads the processing program stored in the memory 4b to execute the processing program, to thereby achieve the functions of the respective sections shown in FIG. 2. However, the processor 4a is not limited to the configuration, but may be configured as a dedicated electronic circuit configured to achieve the functions of the respective sections.

Figure 5:
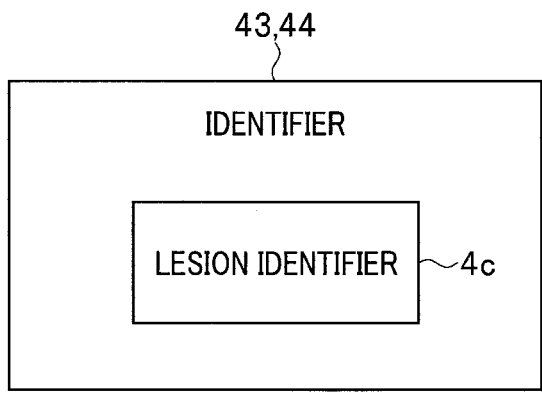
FIG. 5 is a block diagram showing a configuration example of identifiers 43, 44.

FIG. 5 is a block diagram showing a configuration example of the identifiers 43, 44. The white light identifier 43 and the special light identifier 44 each include a lesion identifier 4c configured to detect a region of a lesion candidate from the image information acquired by the illumination light being applied. Note that each of the first special light identifier 45A and the second special light identifier 45B shown in FIG. 3 has the similar configuration as described above. The lesion identifier 4c includes an AI (Artificial Intelligence) that has learned a lesion image, for example.

The image pickup apparatus 21 acquires the white light image information (hereinafter referred to as white light image) and the special light image information (hereinafter referred to as special light image) in sequence, that is, in such a repeated manner as to acquire a white light image again after a special light image.

The image processing section 41 receives the white light images and the special light images acquired in sequence by the image pickup apparatus 21. The image processing section 41 performs various kinds of processing, such as demosaicing, noise correction, color correction, contrast correction, gamma correction, and the like, on the image information outputted from the image pickup apparatus 21, to convert the image information into an image signal (image-for-display information) in a format that can be outputted to the monitor 5.

The region discrimination section 42 discriminates colors in the white light image, to discriminate between a region (or an image) that can be observed in the white light image and a region (or an image) that is difficult to observe in the white light image. The region that can be observed in the white light image is a region including a mucosa, a blood vessel, a lesion, and the like. On the other hand, the region that is difficult to observe in the white light image is a region in which the mucosa, the blood vessel, the lesion, etc., under the bile/residue, the blood, and the like cannot be observed due to the bile/residue, the blood, and the like.

Specifically, the region discrimination section 42 discriminates the colors in the white light image are yellow or red, to thereby discriminate between the region of the mucosa, and the like that can be observed in the white light image and the region of the bile/residue, the blood, and the like that are difficult to observe in the white light image. More specifically, the region discrimination section 42 divides the white light image into predetermined regions, and if a percentage of the yellow color or the red color is less than a specified value in a region of the predetermined regions, the region discrimination section 42 discriminates that the region can be observed in the white light image, and if the percentage of the yellow color or the red color is the specified value or more in a region of the predetermined regions, the region discrimination section 42 discriminates that the region is difficult to observe in the white light image.

The region discrimination section 42 outputs image information of the region that can be observed in the white light image to the white light identifier 43. On the other hand, regarding the region that is difficult to observe in the white light image, the region discrimination section 42 generates image information of a region in the special light image, the region being the same as the region that is difficult to observe in the white light image, to output the generated image information to the special light identifier 44.

The white light identifier 43 that configures a first identifier is an identifier that detects a lesion from the white light image picked up by applying the white light. The white light identifier 43 includes an AI that has learned a lesion image picked up as the white light image, by machine learning, deep learning, etc. The white light identifier 43 detects, in the white light image, whether a lesion candidate (or lesion) is present in the region discriminated by the region discrimination section 42 as the mucosa region that can be observed in the white light image. In addition, the white light identifier 43 calculates a reliability score of the detected lesion candidate. The reliability score indicates an accuracy (certainty degree) that the lesion candidate is actually a lesion.

The special light identifier 44 that configures a second identifier is an identifier that detects a lesion from the special light image picked up by applying the special light that passes through the bile/residue, the blood, and the like (light is not absorbed) which are difficult to observe in the white light image. The special light identifier 44 includes an AI that has learned a lesion image picked up as the special light image, by machine learning, deep learning, etc. The special light identifier 44 detects, in the special light image, whether a lesion candidate (or a lesion) is present in the region that is difficult to observe by using the white light. In addition, the special light identifier 44 calculates a reliability score of the detected lesion candidate.

Note that the special light that passes through the bile/residue is different from the special light that passes through the blood. Therefore, the learning data for the bile/residue is also different from that for the blood. The special light identifier 44 is configured to perform learning by adaptively switching the learning data for the bile/residue and the learning data for the blood. Note that, as shown in the configuration in FIG. 3, an identifier may be provided for each special light.

Specifically, the endoscope processor 4A includes the first special light identifier 45A and the second special light identifier 45B. The first special light identifier 45A is an identifier that detects a lesion from a first special light image picked up by applying the first special light which is emitted from the first special light source 33 and which passes through the bile/residue. The second special light identifier 45B is an identifier that detects a lesion from the second special light image picked up by applying the second special light which is emitted from the second special light source 34 and which passes through the blood.

In this case, the first special light identifier 45A is an identifier that detects a lesion from the first special light image. The first special image is acquired by applying the first special light that passes through the bile/residue (only the light in the green wavelength band and the light in the red wavelength band, except for the light in the blue wavelength band, are used, to thereby enable the mucosa to be observed through the bile/residue). The first special light identifier 45A includes an AI that has learned, by machine learning, deep learning, or the like, a lesion image picked up as the first special light image in which the bile/residue is made transparent.

The second special light identifier 45B is an identifier that detects a lesion from the second special light image. The second special light image is acquired by applying the second special light that passes through the blood (amber light and light in the red wavelength band, each having a peak around 600 nm, are used, to thereby enable the mucosa to be observed through the thin blood). The second special light identifier 45B includes an AI that has learned, by machine learning, deep learning, or the like, a lesion image picked up as the second special light image in which the blood is made transparent.

The display processing section 46 combines pieces of image information received via the white light identifier 43 and the special light identifier 44, to generate a partial transparent image to be described later, and outputs a video signal to the monitor 5. In addition, the display processing section 46 performs, on the partial transparent image, image synthesizing processing for displaying the lesion information (presence or absence of the lesion, position of the lesion) detected by the white light identifier 43 and/or special light identifier 44, to output the video signal to the monitor 5.

The bus 47 is a transmission path through which instructions and information are transmitted and received by the respective sections in the endoscope processor 4.

The control section 48 is connected, via the bus 47, to the image processing section 41, the region discrimination section 42, the white light identifier 43, the special light identifier 44, and the display processing section 46, to control these components.

Figure 6:
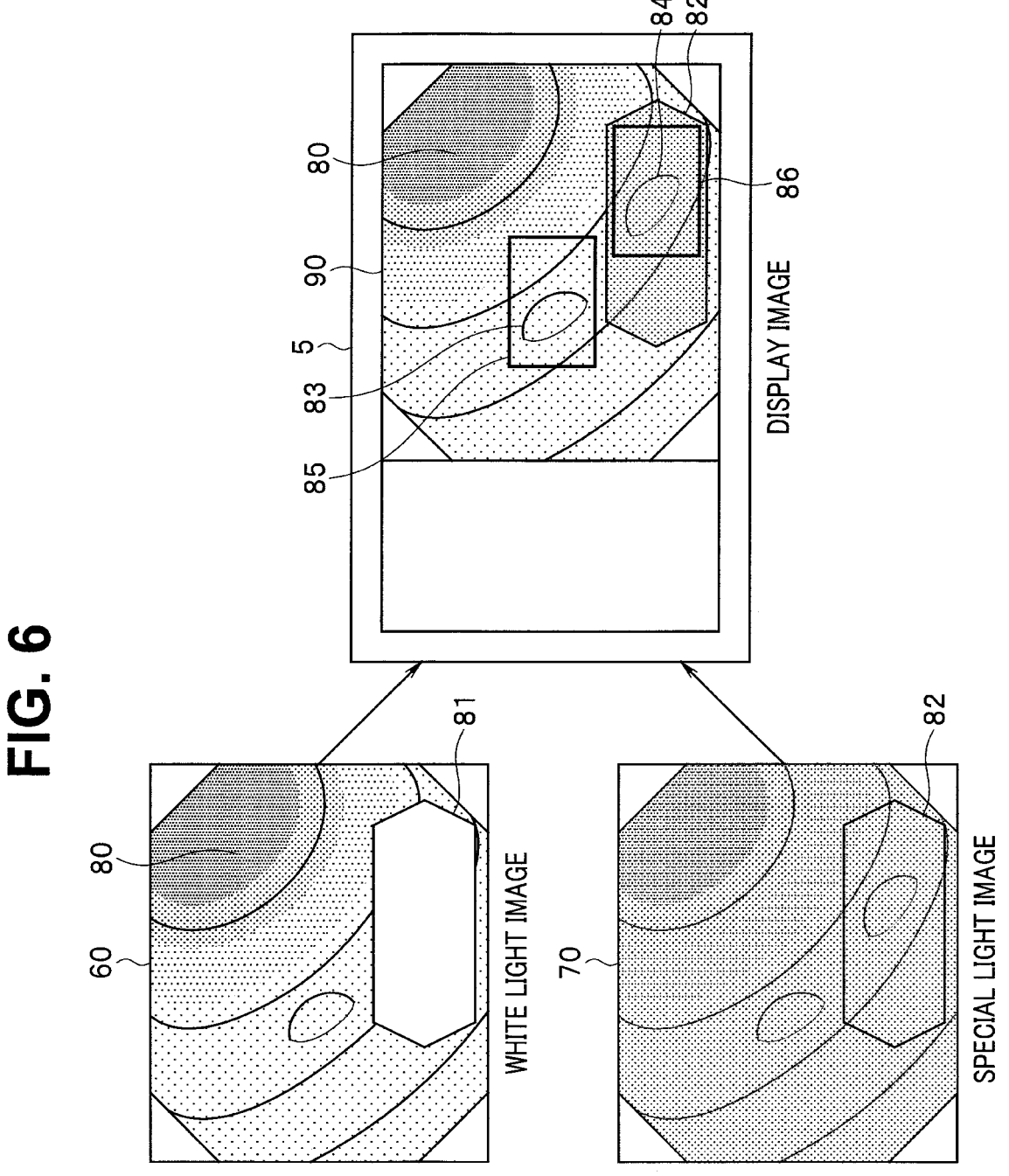

Next, description will be made on display processing by the endoscope processor 4 with reference to FIG. 6. FIG. 6 is a view showing an example of the display processing in a case where the white light image includes the residue, the blood, and the like.

The region discrimination section 42 discriminates, in the white light image 60 acquired by applying the white light as the first illumination light, between first region image information (hereinafter, referred to as a first region image) 80 and second region image information (hereinafter, referred to as a second region image) 81. The first region image includes an object of an interest subject such as the mucosa, the blood vessel, the lesion, and the like. The second region image includes an object of a non-interest subject such as the residue, the blood, and the like. In other words, the first region image 80 is an image of the region in which the mucosa, the blood vessel, the lesion, and the like can be observed with the white light. The second region image 81 is an image of the region in which the mucosa, the blood vessel, the lesion, and the like cannot be observed with the white light. The region discrimination section 42 outputs to the white light identifier 43 the first region image 80 that can be observed with the white light.

Furthermore, the region discrimination section 42 generates third region image information (hereinafter, referred to as a third region image) 82 of a region in the special light image 70 acquired by applying the special light as the second illumination light, the region being the same as the region of the second region image. The region discrimination section 42 outputs, to the special light identifier 44, the third region image 82 in which the residue, the blood, and the like are made transparent by the special light.

The white light identifier 43 uses the AI for the first region image 80 to detect a lesion candidate and calculate a reliability score. The white light identifier 43 outputs the first region image 80, in addition to the detected lesion candidate and the calculated reliability score, to the display processing section 46.

The special light identifier 44 uses the AI for the third region image to detect a lesion candidate and calculate a reliability score. The special light identifier 44 outputs the third region image 82, in addition to the detected lesion candidate and the calculated reliability score, to the display processing section 46.

The display processing section 46 combines the first region image 80 and the third region image 82, to generate partial transparent image information (hereinafter, referred to as a partial transparent image) 90 in which the residue, the blood, and the like, which are the objects of non-interest subjects, in the white light image 60 are made transparent. In addition, in a case where a lesion candidate 83 is detected in the first region image 80 and a lesion candidate 84 is detected in the third region image 82, the display processing section 46 displays markers 85 and 86 respectively on the lesion candidate 83 and the lesion candidate 84. The markers 85 and 86 each indicate the position, the size, etc., of each of the lesion candidates 83 and 84.

Figure 7:
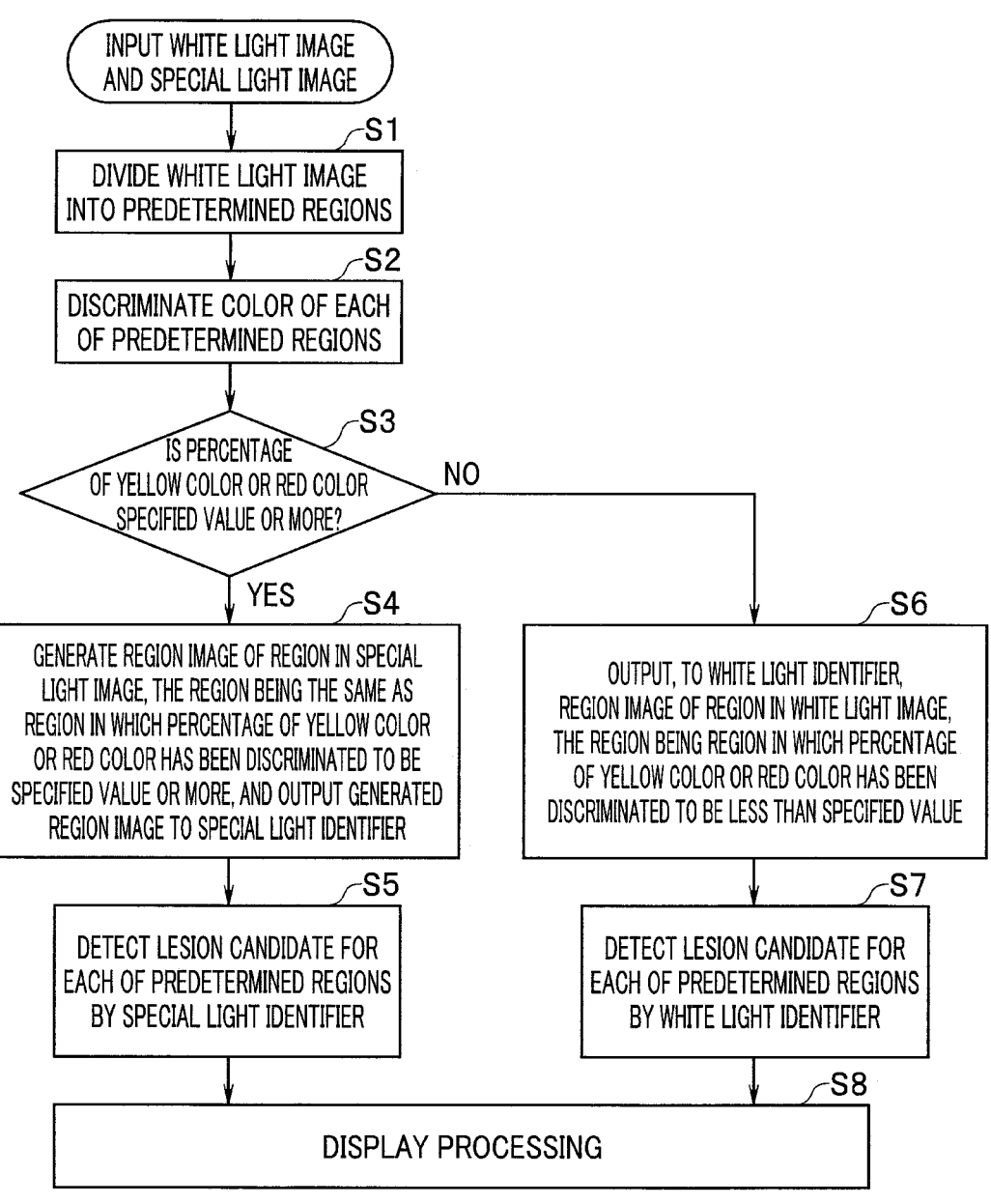
FIG. 7 is a flowchart showing processing by the endoscope processor 4.

FIG. 7 is a flowchart showing the processing by the endoscope processor 4. Note that the processing in FIG. 7 is repeatedly executed while the images picked up by the image pickup apparatus 21 are being inputted into the endoscope processor 4.

The light source apparatus 3 emits light by sequentially switching between the white light and the special light, to thereby cause the white light image and the special light image to be picked up alternately by the image pickup apparatus 21, and then to be inputted to the image processing section 41 of the endoscope processor 4. Then, the white light image and the special light image are subjected to image processing in the image processing section 41, to be inputted to the region discrimination section 42.

The region discrimination section 42 divides the white light image into predetermined regions (S1), and discriminates the color of each of the predetermined regions of the divided white light image (S2).

Next, the region discrimination section 42 discriminates, for each of the predetermined regions, whether the percentage of the yellow color or the red color is the specified value or more (S3). If the region discrimination section 42 discriminates that the percentage of the yellow color or the red color is the specified value or more for each of the predetermined regions, the region discrimination section 42 generates a region image of a region in the special light image, the region being the same as the region in which percentage of the yellow color or the red color has been discriminated to be the specified value or more, and outputs the generated region image to the special light identifier 44 (S4). The special light identifier 44 detects a lesion candidate for each of the predetermined regions (S5). The special light identifier 44 outputs the received region image and the detected lesion candidate to the display processing section 46.

On the other hand, if the region discrimination section 42 discriminates that the percentage of the yellow color or the red color is less than the specified value, the region discrimination section 42 outputs, to the white light identifier 43, the region image of the region in the white light image, the region being the region in which the percentage of the yellow color or the red color has been discriminated to be less than the specified value (S6). The white light identifier 43 detects a lesion candidate for each of the predetermined regions (S7). The white light identifier 43 outputs the received region image and the detected lesion candidate to the display processing section 46.

The display processing section 46 generates the partial transparent image by combining the respective region images, to perform display processing for displaying the partial transparent image on the monitor 5 (S8). With such a display processing, the partial transparent image in which the residue, the blood, and the like are made transparent is displayed on the monitor 5. In addition, in the case where the lesion candidate is detected by the processing in S5 and/or S7, the display processing section 46 performs, in the processing in S8, display processing for displaying the marker on the lesion candidate.

As described above, regarding the region image (first region image) including the yellow color or the red color, the percentage of which is less than the specified value, the endoscope processor 4 inputs the white light image to the white light identifier 43 to detect the lesion, and regarding the region image (second region image) including the yellow color or the red color, the percentage of which is the specified value or more, the endoscope processor 4 inputs, to the special light identifier 44, the region image (third region image) in the special light image, the third region image being the image of the same region as that in the second region image, to detect the lesion.

Then, the endoscope processor 4 combines the first region image and the third region image, to thereby generate the partial transparent image in which the residue, the blood, and the like in the white light image are made transparent. As a result, the endoscope processor 4 is capable of achieving the function for detecting the lesion without removing the residue and the blood.

SECOND EMBODIMENT

In the first embodiment, the white light and the special light are alternately emitted, to acquire the white light image and the special light image. In contrast, the second embodiment is different from the first embodiment in that the special light is emitted to acquire a special light image when it is judged that observation is difficult in the white light image.

FIG. 8 is a block diagram showing an example of a configuration of an endoscope apparatus 1 according to the second embodiment. Note that, in FIG. 8, the same constituent elements as those in FIG. 2 are attached with the same reference signs and description thereof will be omitted.

An endoscope processor 4B is configured by using a region discrimination section 42A and a control section 48A, instead of the region discrimination section 42 and the control section 48 in FIG. 2. If the region discrimination section 42A discriminates that there is a second region image 81 in which detection of a lesion or the like is difficult due to residue, blood, and the like in the white light image picked up by using white light, the region discrimination section 42A outputs the discrimination result to the control section 48A. Specifically, the region discrimination section 42A divides the white light image into predetermined regions, to discriminate, for each of the predetermined regions, whether a percentage of yellow color or red color is a specified value or more. If the region discrimination section 42A discriminates that the percentage of the yellow color or the red color is the specified value or more, the region discrimination section 42A outputs, to the control section 48A, the discrimination result indicating the presence of the second region image in which detection of a lesion or the like is difficult. In the case where the second region image is present, the region discrimination section 42A outputs, to the white light identifier 43, the first region image in which the lesion or the like can be detected in the white light image.

When receiving the discrimination result indicating the presence of the second region image, the control section 48A controls the light source apparatus 3 to emit special light. In other words, the control section 48A controls the light source apparatus 3 to emit the white light in the normal state, and in the case where the control section 48A receives, from the region discrimination section 42A, the discrimination result indicating the presence of the second region image, the control section 48A controls the light source apparatus 3 to emit the special light.

In response to the control by the control section 48A, the light source apparatus 3 emits light by switching from the white light to the special light. Then, the special light image picked up by the image pickup apparatus 21 is inputted to the processor 4A. The region discrimination section 42A generates a third region image in the received special light image, the third region image being the image of the same region as that in the second region image, to output the generated third region image to the special light identifier 44.

The operations of the white light identifier 43, the special light identifier 44, and the display processing section 46 are the same as those in the first embodiment, and the partial transparent image 90 shown in FIG. 6 is displayed on the monitor 5.

Figure 9:
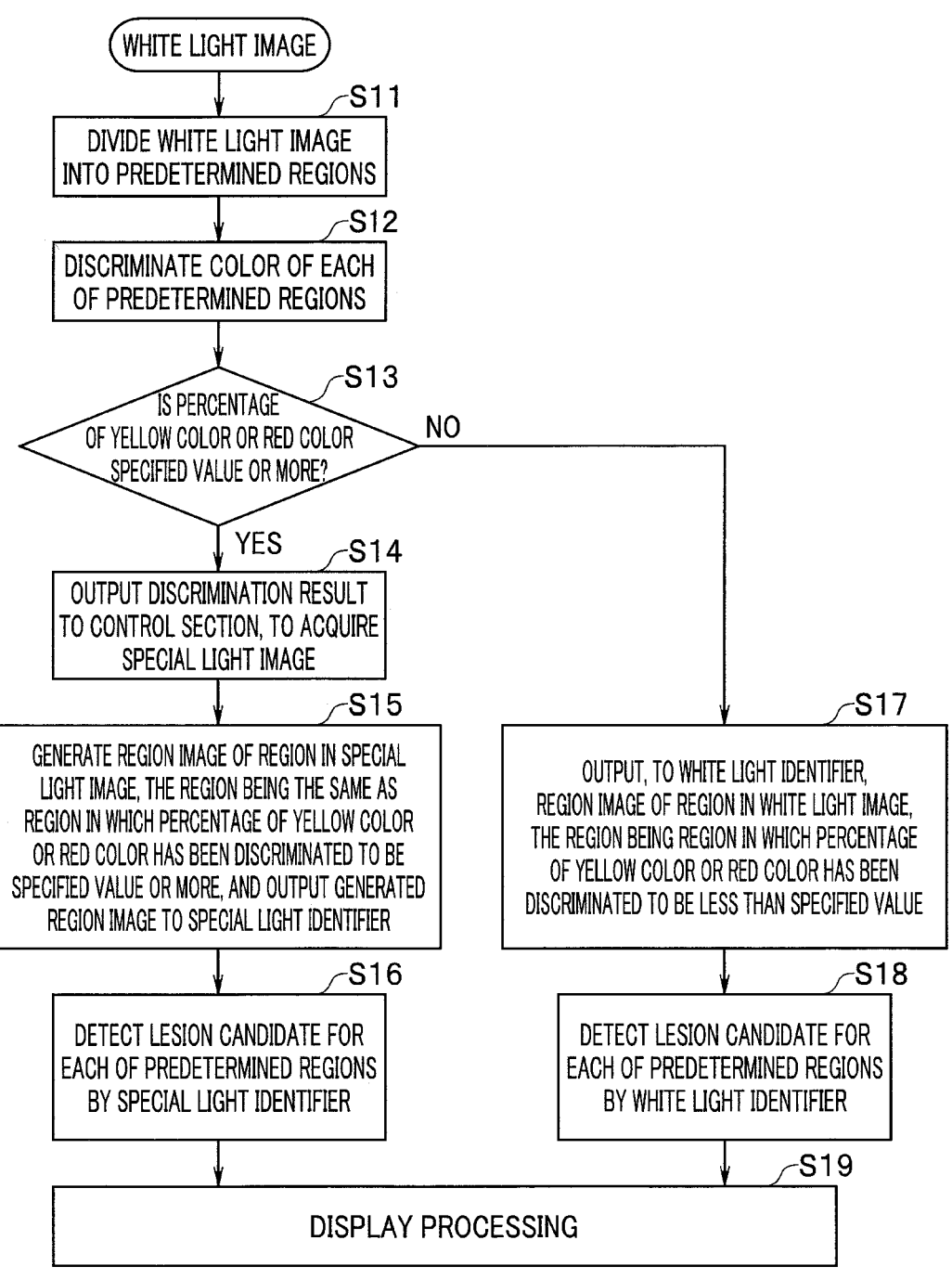
FIG. 9 is a flowchart showing processing by an endoscope processor 4B.

FIG. 9 is a flowchart showing the processing by the endoscope processor 4B. The processing in FIG. 9 is repeatedly executed while the images picked up by the image pickup apparatus 21 are being inputted into the endoscope processor 4B.

The light source apparatus 3 emits the white light, to thereby cause the white light image to be picked up by the image pickup apparatus 21, and inputted to an image processing section 41 of the endoscope processor 4B. Then, the white light image is subjected to image processing in the image processing section 41, to be inputted to the region discrimination section 42A.

The region discrimination section 42A divides the white light image into predetermined regions (S11), and discriminates the color of each of the predetermined regions of the divided white light image (S12).

Next, the region discrimination section 42A discriminates, for each of the predetermined regions, whether the percentage of the yellow color or the red color is the specified value or more (S13). If the region discrimination section 42A discriminates that the percentage of the yellow color or the red color is the specified value or more for each of the predetermined regions, the region discrimination section 42A outputs the discrimination result to the control section 48A, to acquire the special light image (S14). The region discrimination section 42A generates a region image of a region in the acquired special light image, the region being the same as the region in which the percentage of the yellow color or the red color has been discriminated to be the specified value or more, and outputs the generated region image to the special light identifier 44 (S15). The special light identifier 44 detects a lesion candidate for each of the predetermined region (S16). The special light identifier 44 outputs the received region image and the detected lesion candidate to the display processing section 46.

On the other hand, if the region discrimination section 42A discriminates that the percentage of the yellow color or the red color is less than the specified value, the region discrimination section 42A outputs, to the white light identifier 43, the region image of the region in the white light image, the region being the region in which the percentage of the yellow color or the red color has been discriminated to be less than the specified value (S17). The white light identifier 43 detects a lesion candidate for each of the predetermined regions (S18). The white light identifier 43 outputs the received region image and the detected lesion candidate to the display processing section 46.

The display processing section 46 generates a partial transparent image by combining the respective region images and performs display processing for displaying the generated partial transparent image on the monitor 5 (S19). In addition, in the case where the lesion candidate is detected by the processing in S16 and/or S18, the display processing section 46 performs, in the processing in S19, display processing for displaying a marker on the lesion candidate.

With the above-described processing, similarly as in the first embodiment, the endoscope processor 4B can display, on the monitor 5, the partial transparent image in which the residue, the blood, and the like are made transparent.

THIRD EMBODIMENT

In the first and second embodiments, each of the region discrimination sections 42 and 42A discriminates the color of each of the predetermined regions of the white light image, to discriminate whether the region image is the image of the region that is difficult to observe. In contrast, the third embodiment is different from the first and second embodiments in that the discrimination is made based on a reliability score (certainty degree) of lesion discrimination by the white light identifier 43 and the special light identifier 44.

Figure 10:
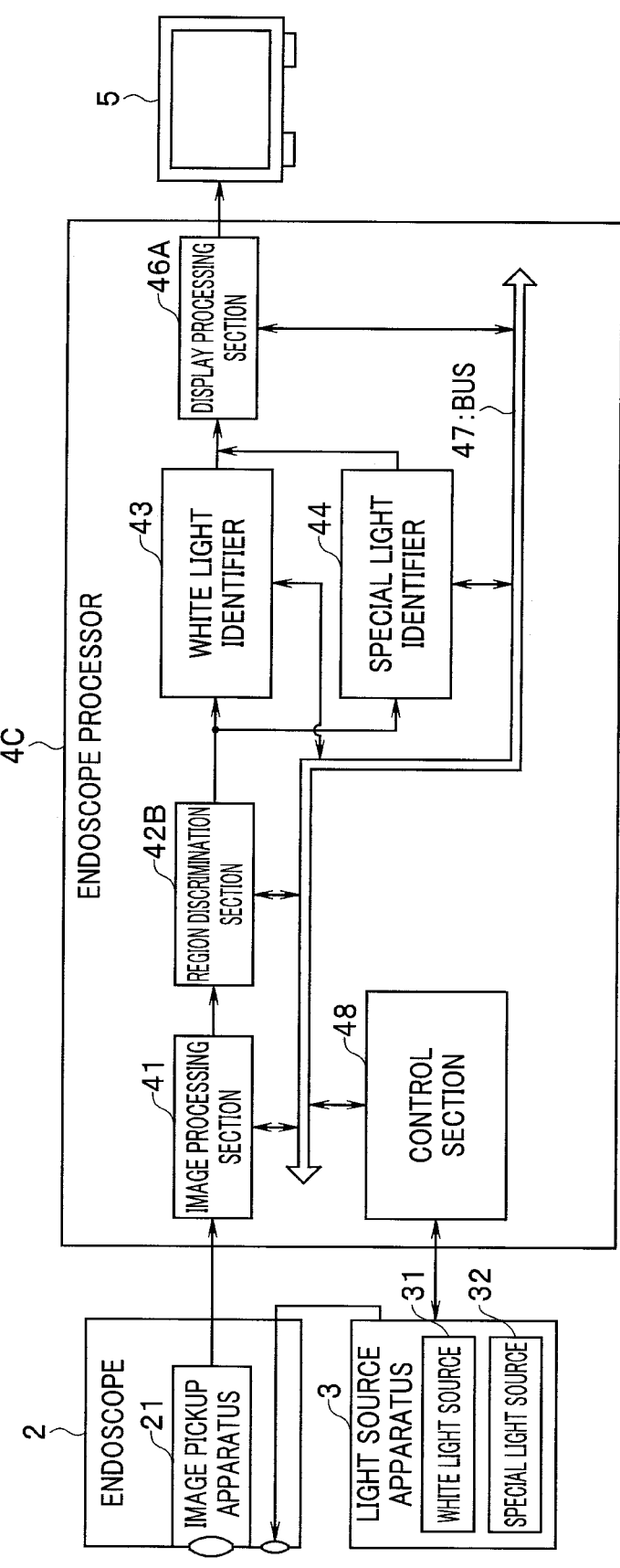
FIG. 10 is a block diagram showing an example of a configuration of an endoscope apparatus 1 according to a third embodiment of the present invention.

FIG. 10 is a block diagram showing an example of a configuration of an endoscope apparatus 1 according to the third embodiment. Note that, in FIG. 10, the same constituent elements as those in FIG. 2 are attached with the same reference signs and descriptions thereof will be omitted.

An endoscope processor 4C is configured by using a region discrimination section 42B and a display processing section 46A, instead of the region discrimination section 42 and the display processing section 46 in FIG. 2. The region discrimination section 42B receives a white light image and a special light image. The region discrimination section 42B divides the white light image into predetermined regions, and thereafter outputs the white light image to the white light identifier 43, and divides the special light image into predetermined regions, and thereafter outputs the special light image to the special light identifier 44.

The white light identifier 43 detects a lesion candidate and calculate a reliability score for each of the predetermined regions of the divided white light image. The white light identifier 43 outputs a detection result of the lesion candidate and a calculation result of the reliability score to the display processing section 46A. The special light identifier 44 detects a lesion candidate and calculate a reliability score for each of the predetermined regions of the divided special light image. The special light identifier 44 outputs a detection result of the lesion candidate and a calculation result of the reliability score to the display processing section 46A.

The display processing section 46A compares the reliability scores for each of the same corresponding regions in the white light image divided into the predetermined regions and the special light image divided into the predetermined regions, and displays the region having a high reliability score.

Figure 11:
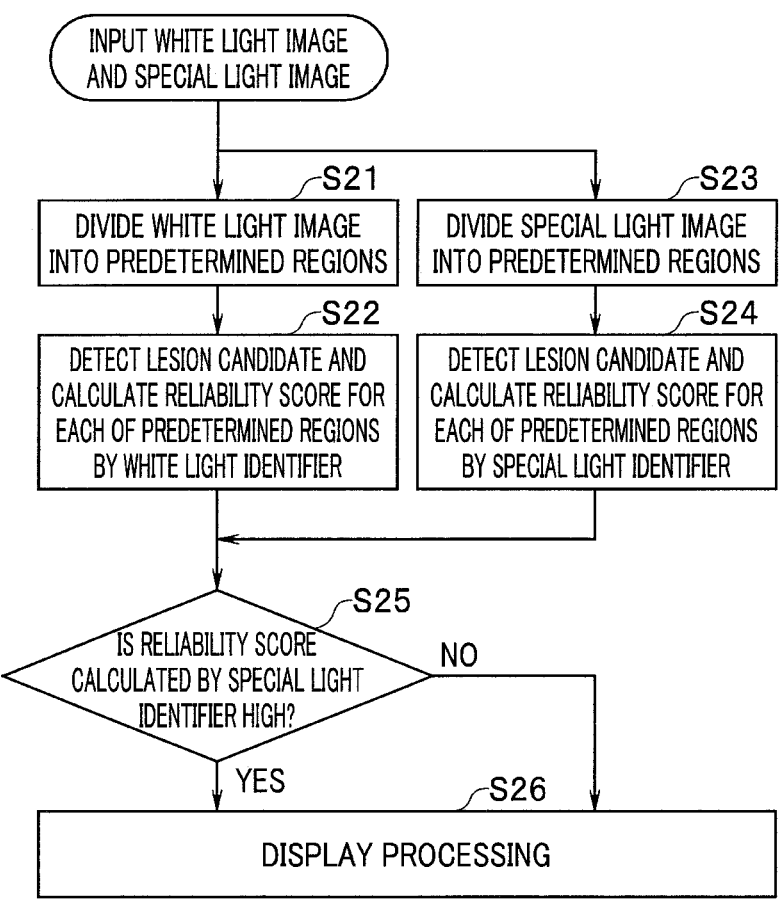
FIG. 11 is a flowchart showing processing by an endoscope processor 4C.

FIG. 11 is a flowchart showing the processing by an endoscope processor 4C. The processing in FIG. 11 is repeatedly executed while the images picked up by the image pickup apparatus 21 are being inputted into the endoscope processor 4C.

The light source apparatus 3 emits light while sequentially switching between the white light and the special light, to thereby cause the white light image and the special light image to be alternately picked up by the image pickup apparatus 21, and to be inputted to an image processing section 41 of the endoscope processor 4C. Then, the white light image and the special light image are subjected to image processing in the image processing section 41, to be inputted to the region discrimination section 42B.

The region discrimination section 42B divides the white light image into predetermined regions (S21), and thereafter outputs the white light image to the white light identifier 43. The white light identifier 43 detects a lesion candidate and calculates a reliability score for each of the predetermined regions (S22). Information on the lesion candidate and the reliability score is inputted to the display processing section 46A.

In addition, the region discrimination section 42B divides the special light image into predetermined regions (S23), and thereafter outputs the special light image to the special light identifier 44. The special light identifier 44 detects a lesion candidate and calculates a reliability score for each of the predetermined regions (S24). Information on the lesion candidate and the reliability score is inputted to the display processing section 46A.

The display processing section 46A determines whether the reliability score calculated by the special light identifier 44 is high (S25). The display processing section 46A performs display processing so as to select and display the predetermined region of the special light image if determining that the reliability score calculated by the special light identifier 44 is high, and to select and display the predetermined region of the white light image if determining that the reliability score calculated by the special light identifier 44 is not high (S26). In addition, in the case where the lesion candidate is detected by the processing in S22 and/or S24, the display processing section 46A performs, in the processing in S26, display processing for displaying a marker on the lesion candidate.

With the above-described processing, similarly as in the first embodiment, the endoscope processor 4C can display, on the monitor 5, the partial transparent image in which the residue, the blood, and the like are transparent.

FOURTH EMBODIMENT

In the first to third embodiments, one image is divided into regions and discrimination is made for each of the regions. In contrast, in the fourth embodiment, discrimination is made in a unit of an image.

Figure 12:
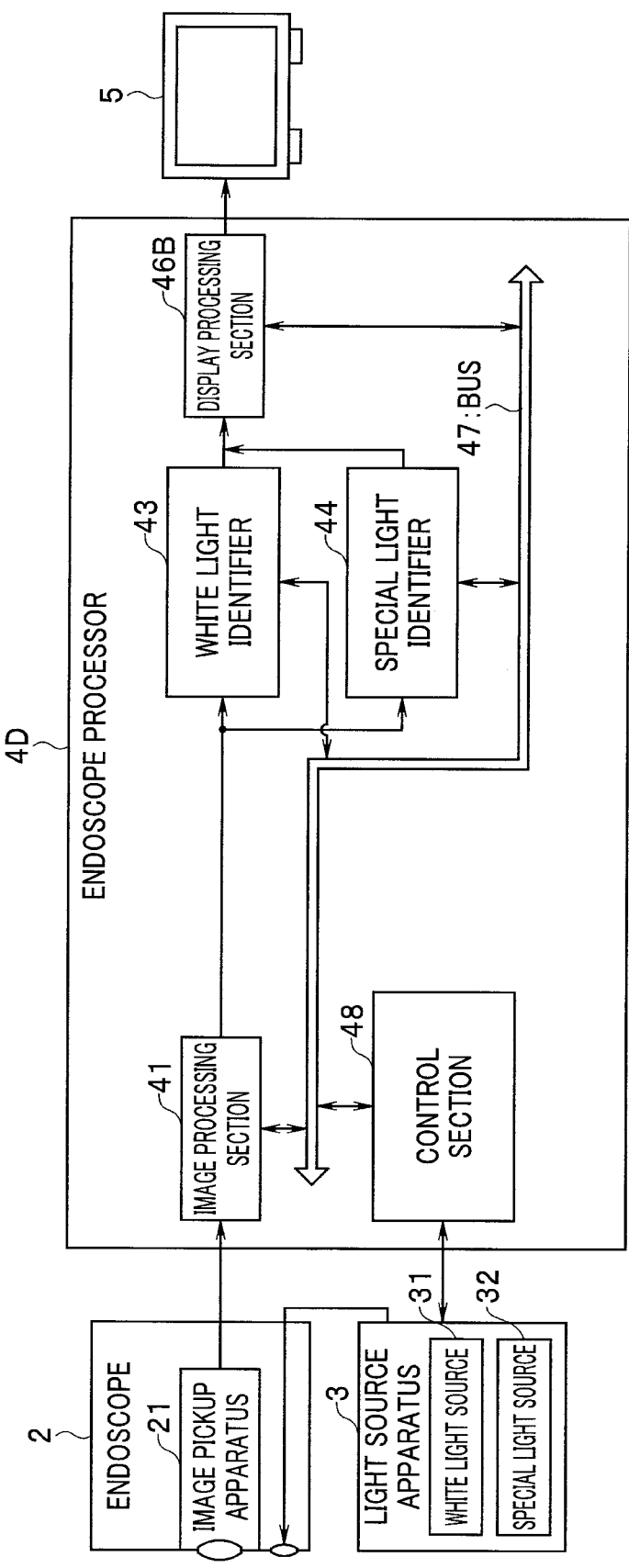
FIG. 12 is a block diagram showing an example of a configuration of an endoscope apparatus 1 according to a fourth embodiment of the present invention.

FIG. 12 is a block diagram showing an example of a configuration of an endoscope apparatus 1 according to the fourth embodiment. Note that, in FIG. 12, the same constituent elements as those in FIG. 2 are attached with the same reference signs and descriptions thereof will be omitted.

An endoscope processor 4D is configured by removing the region discrimination section 42 in FIG. 2, and by including a display processing section 46B instead of the display processing section 46.

The image processing section 41 outputs a white light image and a special light image respectively to the white light identifier 43 and the special light identifier 44. The white light identifier 43 detects a lesion candidate and calculates a reliability score from the white light image and outputs the detected lesion candidate and the calculated reliability score to the display processing section 46B. The special light identifier 44 detects a lesion candidate and calculates a reliability score from the special light image and outputs the detected lesion candidate and the calculated reliability score to the display processing section 46B.

The display processing section 46B determines whether the reliability score calculated by the special light identifier 44 is high. If determining that the reliability score calculated by the special light identifier 44 is high, the display processing section 46B performs display processing so as to display the special light image on the monitor 5. On the other hand, if determining that the reliability score calculated by the special light identifier 44 is not high, the display processing section 46B performs display processing so as to display the white light image on the monitor 5.

Figure 13:
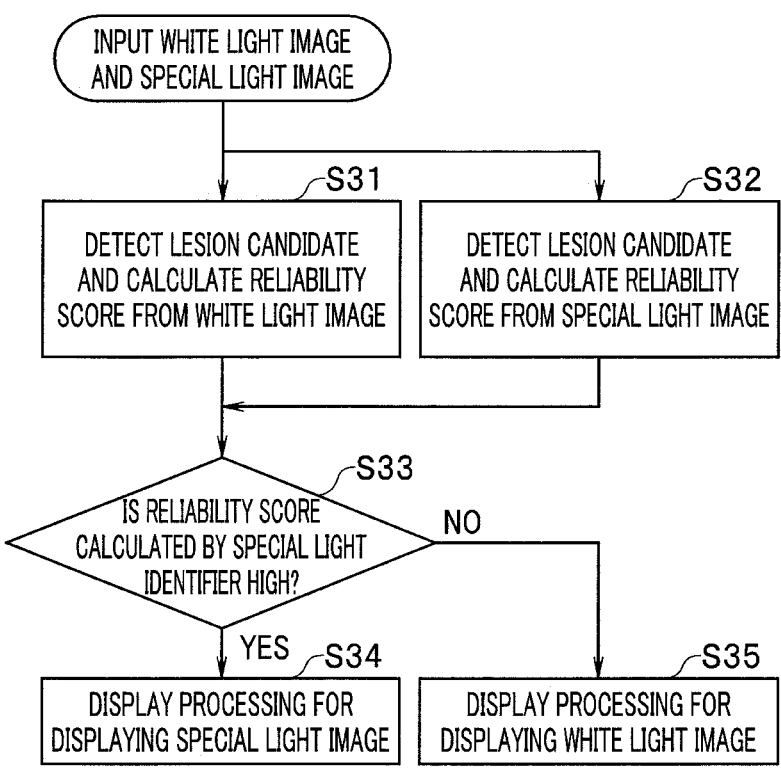
FIG. 13 is a flowchart showing processing by an endoscope processor 4D.

FIG. 13 is a flowchart showing the processing by an endoscope processor 4D. The processing in FIG. 13 is repeatedly executed while the images picked up by the image pickup apparatus 21 are being inputted into the endoscope processor 4D.

The light source apparatus 3 emits light while sequentially switching between the white light and the special light, to thereby cause the white light image and the special light image to be picked up alternately by the image pickup apparatus 21, and to be inputted to an image processing section 41 of the endoscope processor 4D. Then, the white light image and the special light image are subjected to image processing in the image processing section 41, to be inputted respectively to the white light identifier 43 and the special light identifier 44.

The white light identifier 43 detects the lesion candidate and calculates the reliability score from the white light image (S31). The information on the detected lesion candidate and the calculated reliability score is inputted to the display processing section 46B. The special light identifier 44 detects the lesion candidate and calculates the reliability score from the special light image (S32). The information on the detected lesion candidate and the calculated reliability score is inputted to the display processing section 46B.

The display processing section 46B determines whether the reliability score calculated by the special light identifier 44 is high (S33). If determining that the reliability score calculated by the special light identifier 44 is high, the display processing section 46B performs display processing for displaying the special light image (S34). In addition, in the case where the lesion candidate is detected by the processing in S32, the display processing section 46B performs, in the processing in S34, display processing for displaying a marker on the lesion candidate.

On the other hand, if determining that the reliability score calculated by the special light identifier 44 is not high, the display processing section 46B performs display processing for displaying the white light image (S35). In addition, in the case where the lesion candidate is detected by the processing in S31, the display processing section 46B performs, in the processing in S35, display processing for displaying a marker on the lesion candidate.

With such processing, the endoscope processor 4D can display, on the monitor 5, one of the white light image and the special light image, in which it is more likely to observe the lesion candidate.

FIFTH EMBODIMENT

In the first to fourth embodiments, the position of the lesion is detected and displayed. In contrast, the fifth embodiment is different from the first to fourth embodiments in that a distinguishing result of a lesion is displayed.

Figure 14:
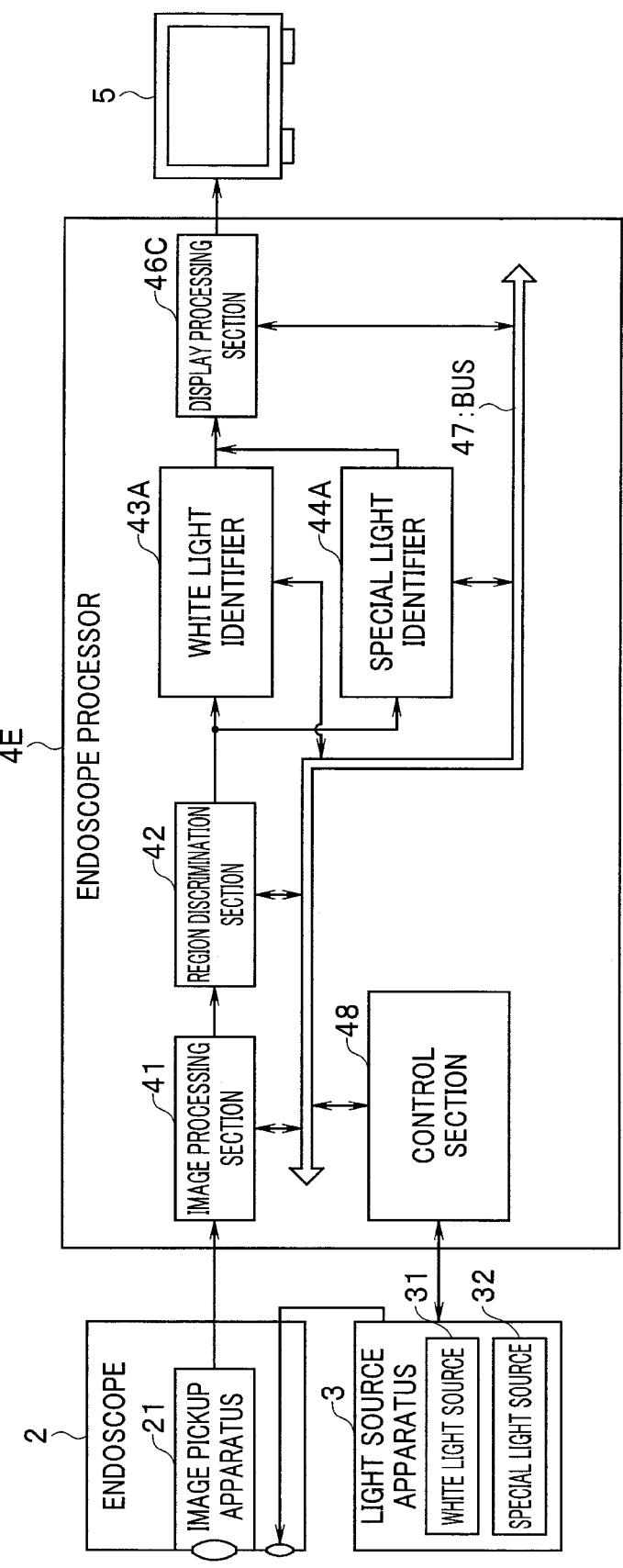
FIG. 14 is a block diagram showing an example of a configuration of an endoscope apparatus 1 according to a fifth embodiment of the present invention.

FIG. 14 is a block diagram showing an example of a configuration of an endoscope apparatus 1 according to the fifth embodiment. Note that, in FIG. 14, the same constituent elements as those in FIG. 2 are attached with the same reference signs and descriptions thereof will be omitted.

An endoscope processor 4E is configured by including a white light identifier 43A, a special light identifier 44A, and a display processing section 46C, instead respectively of the white light identifier 43, the special light identifier 44, and the display processing section 46 in FIG. 2.

Each of the white light identifier 43A and the special light identifier 44A is caused to learn distinguishing information on a lesion as well as a lesion image. With such learning, the white light identifier 43A and the special light identifier 44A not only can detect lesion candidates but also can output the distinguishing information (distinguishing result) in descending order of the reliability scores (certainty degrees).

Figure 15:
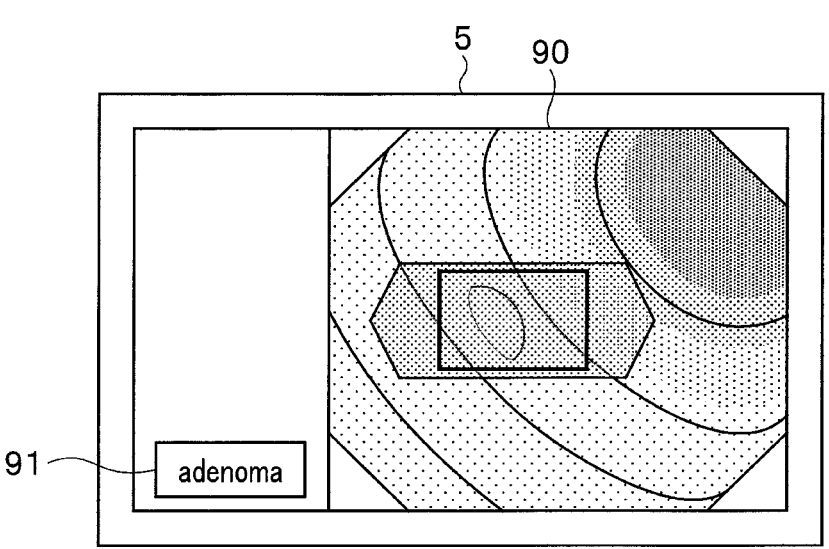
FIG. 15 is a view showing an example of a display screen displayed on a monitor by display processing.
Figure 16:
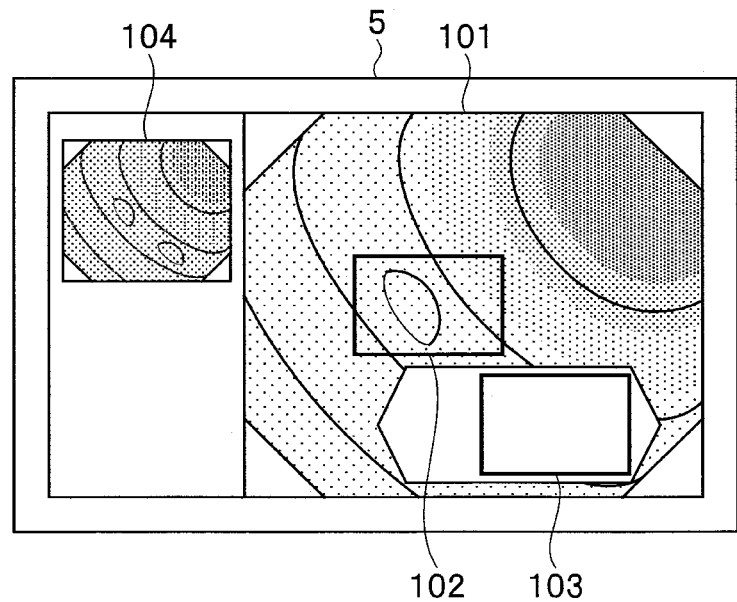
FIG. 16 is a view showing another example of the display screen displayed on the monitor by the display processing.

FIG. 15 is a view showing an example of a display screen displayed on a monitor by display processing, and FIG. 16 is a view showing another example of the display screen displayed on the monitor by the display processing.

The display processing section 46C displays the distinguishing information together with the image in which the lesion can be observed. The display processing section 46C, as shown in FIG. 15, displays an image (white light image or special light image) in which the lesion candidate is detected and also displays distinguishing information 91 with high reliability score adjacently to the image. Note that, in the example in FIG. 15, the display processing section 46C displays one disease name as the distinguishing information 91. However, the distinguishing information 91 is not limited to the example, but a plurality of disease names and probabilities of the respective disease names may be displayed. In addition, the display processing section 46C is not limited to display the disease name as the distinguishing information 91, but may display the progress degree of the disease, for example.

In addition, the display processing section 46C may display the white light image and an image in which the lesion is observed. The display processing section 46C, as shown in FIG. 16, for example, displays, on a main screen, a white light image 101 and markers 102, 103 each indicating the position, the size, and the like of the lesion candidate, and displays on a sub screen smaller than the main screen, a special light image 104 in which the lesion candidate is detected. Note that, in a case where the image in which the lesion candidate is detected is the white light image 101, the display processing section 46C does not have to display the special light image 104 on the sub screen.

With such processing, the endoscope processor 4E not only can detect and display the position of the lesion candidate but also can display the distinguishing information on the monitor 5.

Note that regarding the respective steps in each of the flowcharts in the present specification, the execution order may be changed, a plurality of steps may be executed simultaneously, or the steps may be executed in different order for each execution, unless contrary to the features of the present invention.

The present invention is not limited to the above-described embodiments, and it goes without saying that various modifications, combinations, and applications can be implemented without departing from the subject matter of the invention.

What is claimed is:

1. An endoscope system comprising:
a processor configured to:
discriminate, in first image information acquired by applying first illumination light, between first region image information constituted of an object of an interest subject and second region image information constituted of an object of a non-interest subject;
generate third region image information of a region in second image information acquired by applying second illumination light, the region including at least a part of a region of the second region image information, the second illumination light having a wavelength different from a wavelength of the first illumination light and passing through the object of the non-interest subject, wherein the third region image information includes visual information corresponding to a region behind the object of the non-interest subject; and
combine the first region image information and the third region image information to generate a partial transparent display image in which the object of the non-interest subject in the first image information is made transparent.

2. The endoscope system according to claim 1, wherein the first illumination light is white light.

3. The endoscope system according to claim 1, wherein the processor is further configured to:
adopt an AI for the first region image information;
adopt an AI for the third region image information; and
add a detection result to the partial transparent display image.

4. The endoscope system according to claim 1, wherein the processor is further configured to:
detect a lesion candidate in the first region image information;
detect a lesion candidate in the third region image information, wherein the lesion candidate in the third region image information corresponds to the region behind the object of the non-interest subject; and
add a detection result to the partial transparent display image.

5. The endoscope system according to claim 1, wherein the processor divides the first image information into predetermined regions, to discriminate between a first divided image information constituted of the object of the interest subject and second divided image information constituted of the object of the non-interest subject.

6. The endoscope system according to claim 5, wherein the processor discriminates, in the first image information divided into the predetermined regions, information in which a percentage of a predetermined color is less than a predetermined value as the first divided image information, and an information in which the percentage of the predetermined color is the predetermined value or more as the second divided image information.

7. The endoscope system according to claim 4, wherein the processor is further configured to:

calculate a first reliability score for the lesion candidate in the first region image information; and calculate a second reliability score for the lesion candidate in the third region image information.

8. The endoscope system according to claim 4, wherein the processor acquires distinguishing information of the lesion candidate, to display, on a monitor, the distinguish information together with the first image information in which the lesion candidate is detected or the second image information in which the lesion candidate is detected.

9. The endoscope system according to claim 1, wherein the non-interest subject is a bile, residue, or blood.

10. A diagnostic image display method comprising:

discriminating, in first image information acquired by applying first illumination light, between first region image information constituted of an object of an interest subject and second region image information constituted of an object of a non-interest subject;

generating third region image information of a region in second image information acquired by applying second illumination light, the region including at least a part of a region of the second region image information, the second illumination light having a wavelength different from a wavelength of the first illumination light and passing through the object of the non-interest subject, wherein the third region image information includes visual information corresponding to a region behind the object of the non-interest subject; and combining the first region image information and the third region image information to generate a partial transparent display image in which the object of the non-interest subject in the first image information is made transparent.

11. A non-transitory computer-readable storage medium that stores a program, the program causing a computer to execute:

discriminating, in first image information acquired by applying first illumination light, between first region image information constituted of an object of an interest subject and second region image information constituted of an object of a non-interest subject;

generating third region image information of a region in second image information acquired by applying second illumination light, the region including at least a part of a region of the second region image information, the second illumination light having a wavelength different from a wavelength of the first illumination light and passing through the object of the non-interest subject, wherein the third region image information includes visual information corresponding to a region behind the object of the non-interest subject; and combining the first region image information and the third region image information to generate a partial transparent display image in which the object of the non-interest subject in the first image information is made transparent.

12. The endoscope system according to claim 1, further comprising:

a light source apparatus configured to be capable of emitting first illumination light and second illumination light;

an endoscope comprising an image pickup apparatus configured to acquire first image information by the first illumination light being applied and to acquire second image information by the second illumination light being applied; and a monitor configured to display the partial transparent display image.

13. The endoscope system according to claim 1, wherein a range of a visual field of the second image information is larger than a range of a visual field of the third region image information.

14. The endoscope system according to claim 13, wherein the first image information and the third region image information are superimposed to generate the partial transparent display image.

15. The endoscope system according to claim 13, wherein the third region image information includes an entirety of the region of the second region image information.

16. The endoscope system according to claim 15, wherein the third region image information is same as the region of the second region image information.

17. The endoscope system according to claim 1, wherein the first region image information is a region in which a percentage of a yellow color or a red color is less than a specified value, and the second region image information is a region in which the percentage is the specified value or more.

\* \* \* \* \*